CHROMOPHORE BLUE ADSORBENT METHOD FOR THE PURIFICATION OF PREPARATIONS HAVING AN INTERFERON TYPE ACTIVITY

The invention is concerned with a process for the purification of preparations having a therapeutic activity, and in particular an interferon-type activity.

It also embraces the corresponding purified preparations and their use as the active ingredient of medicines.

It is known that interferon is a therapeutic product of great value, and specifically by reason of its remarkable anti-viral and immuno-depressive properties.

According to the usual methods of synthesis in vitro, this product is obtained by the action of virus or of chemical substances upon tissue cultures. The resultant preparations however also contain contaminating substances. Specifically, such preparations contain proteins which have a pyrogenous action and besides display inconvenient ability to induce a specific sensitisation in the recipient.

Consequently the crude interferon preparations cannot be used directly, in particular for the applications envisaged hereinabove, and must be purified.

Various methods have been suggested, specifically methods for purification by filtration through gel or through ion exchangers.

The use of these methods for the purification of interferon preparations however runs up against difficulties specifically due to very small yields.

Methods of affinity chromatography have also been suggested.

As is known these methods are based upon a selective affinity between an adsorbing phase constituted by a ligand fixed in covalent manner upon a solid support and some given product. The passage of a preparation containing the product through the adsorbing phase enables the product to be retained in a selective manner upon the ligand and thus enables it to be separated from the preparation containing it. The recovery of the product thus fixed can then be achieved with the help of an appropriate eluant.

The use of these particular techniques for the purification of interferon preparations however runs up against difficulties, and the attempts carried out up to the present time have not led to satisfactory results.

Thus the methods of affinity chromatography which, for the purification of the interferon, use anti-interferon specific antibodies have not yet been developed upon a large scale due to the difficulties of manufacturing anti-interferon anti-sera.

The object of the present invention is to remedy these inconveniences and provide a process which will make it possible to obtain, in an extremely simple manner and moreover with excellent yields, interferon preparations which possess a high content of products with interferon-type activity, to a major extent freed from contaminating proteins, and consequently capable of use in therapy.

Another object is to provide purified preparations in aqueous solution and thereby directly capable of use in therapy.

For that purpose, according to the process of the invention a crude preparation of interferon is put in contact with an adsorbent equilibrated with a buffer whose concentration in salts is isomolar or hypomolar relative to that of blood, the said adsorbent comprising on the one hand a gel forming a solid support, the size of the pores in which is such that they permit the passage of macro-molecules, and on the other hand a compound fixed upon the said support, playing the role of ligand vis-a-vis the products which it is desired selectively to separate, and which possesses a polycyclic structure of the kind of the blue chromophore, sold under the Trade Mark BLUE CIBACRON F3GA, of the formula

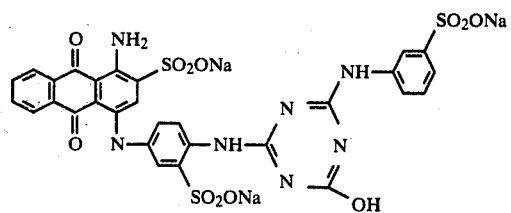

or an equivalent product, whose configuration permits the interferon to be retained in a selective manner, the amount of adsorbent employed and the period of contact between the ligand and the preparation to be purified being sufficient to enable the desired fixation of the products with interferon-type activity from the above-indicated preparations, and that, for recovery of the products thus fixed, one elutes with the help of a buffer whose concentration in salts is hypermolar by comparison with that of blood by contacting the products fixed on the adsorbent with said buffer.

By these means it is possible to separate interferon with remarkable selectivity from preparations containing it, these preparations being either of human or of animal origin and constituted specifically by the supernatent liquids of tissue cultures, either freshly transplanted (primary or secondary cultures) or continuously grown, where the cells have been induced to form interferon, advantageously in a culture medium freed from serum, by a virus or by a synthetic nucleic acid such as poly I.C.

The separated interferon can easily be recovered, in practice in an almost total manner and without it being denatured, by carrying out an elution under the appropriate conditions indicated above. Furthermore, the advantage of this process is increased by the fact that the adsorption capacity of the adsorbent employed is practically undamaged. Consequently, this adsorbent can be reused for numerous purification operations, which is extremely advantageous from the economic view point.

In one embodiment of the invention the gel forming the solid support for the adsorbent comprises a polysaccharide such as agarose or a derivative thereof, specifically a modified agarose in which the polysaccharide chains are cross-linked in a three-dimensional sieve, in particular that sold under Trade Mark SEPHAROSE or again a polyacrylamide or an acrylic resin.

The ligand coupled to the solid support is advantageously provided by CIBACRON BLUE F3GA itself, or the product sold under the Trade Mark CIBACRON BLUE 3 GA (which differs essentially from the previous one by the presence of a hydrogen atom in place of the —SO₂ONa upon the phenyl radical at the extremity of the chain), or again by some equivalent product. By "equivalent product" there is meant, in both the description and the claims, a product which even if it differs from the blue chromophores indicated above in the kind and/or the position of its substitutions never-

United States Patent [19]

De Maeyer et al.

[11] 4,172,071

[45] Oct. 23, 1979

[54] CHROMOPHORE BLUE ADSORBENT METHOD FOR THE PURIFICATION OF PREPARATIONS HAVING AN INTERFERON TYPE ACTIVITY

[75] Inventors: Edward De Maeyer; Jaqueline De Maeyer nee Guignard, both of Orsay, France

[73] Assignee: Agence Nationale de Valorisation de la Recherche (ANVAR), Neuilly sur Seine, France

[21] Appl. No.: 798,523

[22] Filed: May 19, 1977

[30] Foreign Application Priority Data

May 21, 1976 [FR] France .................................. 76 15414

[51] Int. Cl.$^2$ ............................................. A61K 45/02
[52] U.S. Cl. .................................... 260/112 R; 424/85
[58] Field of Search ....................... 260/112 R; 424/85

[56] References Cited

U.S. PATENT DOCUMENTS

| 3,265,581 | 8/1966 | Fantes et al. | 424/85 |
|---|---|---|---|
| 3,414,651 | 12/1968 | Fantes | 424/85 |
| 3,773,924 | 11/1973 | Ho et al. | 424/85 |
| 3,975,344 | 8/1976 | Schwartz | 260/112 R |
| 3,981,991 | 9/1976 | Stewart et al. | 424/85 |
| 4,016,149 | 4/1977 | Travis et al. | 260/122 |
| 4,041,152 | 8/1977 | Chany et al. | 424/85 |

OTHER PUBLICATIONS

Proc. Soc. Exptl. Biol. & Med., vol. 153, No. 3, Dec., 1976, Cesario et al.
Chem. Abstract, vol. 77, 1972, 84911y, Boehme et al.

Primary Examiner—Howard E. Schain
Attorney, Agent, or Firm—Sprung, Felfe, Horn, Lynch & Kramer

[57] ABSTRACT

The invention relates to a process for the purification of preparations having an interferon type-activity which comprises contacting the crude preparations with an adsorbent comprising as ligand a chromophore blue, equilibrated with an aqueous buffer whose concentration in salts is isomolar or hypomolar as compared with that of blood, and separating the fixed products having an interferon activity by using an aqueous buffer whose concentration in salts is hypermolar as compared with that of blood.

The purified preparations thus obtained are used as active ingredients of drugs having antiviral activity.

20 Claims, No Drawings caused by the virus and their inhibitive action against the recurrence of hepatic keratitis.

Moreover, said preparations reduce the frequency and the duration of viral complications more especially the ones resulting from herpes Zoster, as evidenced when carrying out the tests according to Jordan et al. in J. Infect. Dis 130, 56-62, 1974. On the other, they seem to increase the life duration of patients suffering from osteosarcome. Such properties may be evidenced by carrying out tests according to Strander et al. Acto Orthop. Scand. 45 p. 958-959, 1974.

All above tests have clearly demonstrated the perfect innocuousness of the products having interferon-type activity according to the invention, as well as the absence of noxious secondary effects resulting from their administration.

Moreover, considering the high degree of purity of the preparations purified according to the invention, the latter will advantageously utilized as active principles of drugs (medicines).

The interferon being specific of the species, it is then necessary for therapeutic applications for example in man to have interferon originating from humain cells.

The medicaments of the invention, which contain said purified preparations as active ingredients, can be administered, more especially by the intramuscular or sub-cutaneous route, in the form of an aqueous solution. A unit posological dose of $10^6$ to $10^8$ can be employed.

The treatment of chronical hepatitis is indicated as an example: patients are administered a $10^7$ units dosis of fibroblaste interferon at alternate days, during two weeks.

Osteosarcomes may be treated by administering $3 \times 10^6$ units dosis of leucocyte interferon three times a week for periods which may range from 6 months to 1 year.

In order that the invention and its advantages may be well understood it will now be described in further detail, though only by way of illustration, in the following Examples:

EXAMPLE 1

Preparation of a BLUE DEXTRAN SEPHAROSE Affinity Column for Purification of Interferon of animal and Human Origin 1. Preparation of BLUE DEXTRAN SEPHAROSE gel The process for manufacture of BLUE DEXTRAN SEPHAROSE gels has been described by L. D. Ryan and C. S. Vestling (*Arch. Biochem. Biophys.*, [1974], 160, 279-284). Since that publication, it has become no longer necessary to undertake the activation of the SEPHAROSE by cyanogen bromide according to Cuatrecasas (P. Cuatrecasas, *J. Biol. Chem.*, [1970], 3059-3065) because there are ready lyophilised commercial preparations for the employment of already activated SEPHAROSE.

One employs SEPHAROSE 4B activated with cyanogen bromide and BLUE DEXTRAN 2000, such as those sold by Pharmacia (Uppsala, Sweden).

(a) Preparation of the SEPHAROSE gel (CNBr SEPHAROSE 4B).

In order to swell the gel and to eliminate the bactericidal agents present in the lyophilised preparation, the desired quantity of CNBr-SEPHAROSE is washed on a ground glass filter with a 1 mM solution of HCl, for about a quarter of an hour. The desired quantity of CNBr-SEPHAROSE is worked out upon the basis that one gram of dry product gives about 3.5 ml of gel. For washing one uses 200 ml of HCl 1 mM per gram of dry weight of CNBr-SEPHAROSE. The gel thus formed is immediately coupled with BLUE DEXTRAN 2000.

(b) Coupling of the SEPHAROSE gel with BLUE DEXTRAN 2000.

The quantity of BLUE DEXTRAN necessary for the coupling is worked out upon the basis that one gram of dry weight of SEPHAROSE is capable of fixing from 80 to 100 mg of BLUE DEXTRAN.

This quantity is dissolved in an alkaline buffer having a pH of the order of 8 to 10, especially a 0.4 M carbonate buffer of pH 10 (20 mg of BLUE DEXTRAN 2000 while easily dissolved in one ml of carbonate buffer).

The solution of BLUE DEXTRAN is poured onto the SEPHAROSE gel previously rinsed with 3 or 4 times its volume of 0.4 M carbonate buffer pH 10. The mixture of the gel and the BLUE DEXTRAN is poured into a deep glass flask and subjected to slight agitation, for example with a revolving paddle wheel, for about 18 to 24 hours, at a temperature of the order of $+4°$ C., in order to promote the coupling.

After the coupling stage, the BLUE DEXTRAN SEPHAROSE product obtained is rinsed, on a ground glass filter, with an excess of 0.4 M carbonate buffer pH 10, in order to eliminate any non-fixed BLUE DEXTRAN, until the buffer remains colourless (optical density equal to or less than 0.02).

In order to eliminate the active sites which have not been fixed to the BLUE DEXTRAN, the product of the coupling is then put in contact with a solution of an alkanolamine, particularly 1 M ethanolamine at pH 8, for about two hours at a temperature of $+4°$ C. For this operation, the product of the coupling is preferably transferred from the flask into another container.

To make the gel resistant to variations in pH, in molarity or in anything else, it is then subjected to three rinsing cycles, each cycle consisting of alternate rinsing firstly with an acid solution consisting of a 0.1 M acetate buffer at pH 4.0 to which 1 M NaCl has been added, and secondly with an alkaline solution which consists of a 0.1 M borate buffer at pH 8.5, to which 1 M NaCl has been added.

After these rinsing cycles, the gel is equilibrated with a 10 mM Tris-HCl buffer pH 7.5 to which a bactericidal and anti-septic agent has been added, in particular 0.02% sodium azide.

2. Preparation of the Affinity Chromatography Column

The BLUE DEXTRAN SEPHAROSE is poured into a chromatography column of the appropriate dimensions (it is estimated that one ml is capable of fixing about 8 million International Units of Interferon).

Before the very first use of the column, it is rinsed with 20 times its empty volume of the 10 mM Tris buffer pH 7.5 to which 0.02% of sodium azide has been added.

To eliminate the molecules of BLUE DEXTRAN which might tend to detach themselves, the elution buffer, consisting of the 10 mM Tris-HCl pH 7.5 to which 1 M NaCl has been added, is passed through until the optical density at 254 nm remains at 0.

(In the case of columns of large dimensions, it is recommended to undertake several successive rinsing cycles with the Tris buffer with and without NaCl in order to strengthen the adaptation of the column to variations in pH, in molarity or other variations).

A BLUE DEXTRAN SEPHAROSE column can be used for several months and for numerous cycles of interferon purification provided that it does not become contaminated by bacteria. It is therefore desirable to keep it, outside periods of use, under sodium azide and in the cold, at about +4° C.

Since however sodium azide is toxic for cells, it is then necessary before carrying out fixation of interferon to pass through the column at least three times its empty volume of the Tris-HCl buffer without azide in order to eliminate any trace of that antiseptic.

EXAMPLE 2

Purification of a Human Interferon Preparation by Chromatography on a Column According to Example 1

The interferon preparation to be purified consists of 32 ml of a supernatent liquid from a freshly-transplanted culture of human fibroblasts, induced to produce interferon by poly I.C. The titre is 6250 International Units of Interferon per ml, the content of proteins is 1 mg per ml (the high content of proteins in this preparation is due to the fact that it has been enriched with human albumin for its preservation). The specific activity of the said preparation is thus $6.2 \times 10^4$ International Units of Interferon per mg of protein.

The preparation is dialysed, at a temperature of about +4° C., for fifteen hours, against the equilibration buffer for the column, in this particular case the 0.01 M Tris-HCl pH 7.5.

32 ml of the preparation are passed, at a rate of 1 ml per minute, through a column 1.6 cm in diameter, containing a BLUE DEXTRAN SEPHAROSE gel according to Example 1 up to a height of 10.5 cm. The column is rinsed as a preliminary matter with at least three times its empty volume of buffer without azide. The sorption phase is monitored on a recorder of optical densities or OD at 280 nm.

As soon as all the preparation has permeated into the gel, it is washed by passing through the column from five to eight times the empty volume of the 10 mM Tris-HCl buffer of pH 7.5 in aqueous solution so as to ensure the elimination of non-adsorbed contaminating substances.

A fall in OD is observed, which finally comes to rest at zero.

To recover the interferon, an aqueous solution of 10 mM Tris-HCl of pH 7.5, to which this time there has been added 1 M of NaCl, is made to pass through the column, with an output of 0.5 to 0.7 ml/mn.

Fractions of 6 ml are collected in tubes, whose OD is measured to monitor the adsorption phase. The results obtained with the fractions in tubes numbered 8 to 11 are given hereinafter, in terms of their interferon titre and their content of proteins.

| Tube No. | International Units of interferon/ml | Proteins (μg/ml) | Specific activity |
|---|---|---|---|
| 8 | 6 250 | 250 | |
| 9 | 61 900 | 278 | $2.2 \times 10^6$ |
| 10 | 830 | 160 | |
| 11 | 660 | 80 | |

It is found that the products with interferon-type activity are mainly recovered in tube No. 9. The interferon titre (U.I.F/ml) is ten times greater than that found in the starting material, while the content of proteins is about 25% of that of the crude preparation; the specific activity has been increased by a factor of 36, or other words the preparation which emerges from the BLUE DEXTRAN SEPHAROSE column has been purified 36 times as compared with the crude preparation.

It is found that the recovery of the chromatographed interferon carried on in aqueous medium is complete. In fact, in tube No. 9 some 6 ml were recovered of an interferon whose titre is 61900 units per ml, thus in total 371,400 units of interferon. This compares with the starting material consisting of 32 ml of a preparation containing 6250 units per ml, thus 200,000 units in total.

This example moreover only seeks to show the effectiveness of the method even in the case of a crude preparation of human interferon which was mediocre at the outset, as much because of its slight content of interferon as also because of its artifial contamination with albumin.

After the desorption phase of the products with interferon-type activity, the column is regenerated by causing about ten times its empty volume of the 10 mM Tris-HCl buffer pH 7.5 to which sodium azide has been added at a rate of 0.02% to pass through the column. In this way the column is made ready for re-use and can meanwhile be preserved at low temperature.

After several cycles of use, the gel can be regenerated to remove any traces of proteins which have become fixed thereon, and to do this the column is rinsed with five times its empty volume of 3 M KCl.

The effectiveness of the method for purification of interferon upon BLUE DEXTRAN SEPHAROSE gel is properly illustrated by Example 3, where chromatography is carried out upon a preparation of mouse interferon not previously enriched artificially with further proteins.

EXAMPLE 3

Purification of a Mouse Interferon Preparation by Chromatography on a Column according to Example 1

The interferon preparation to be purified consists of the supernatent liquid of a tissue culture (cells C 243) induced to produce interferon by the virus of Newcastle disease. After inactivation of the virus at pH 2, the supernatent liquid is dialysed against 0.01 M Tris-HCl pH 7.5, for about 14 hours, at a temperature of about +4° C.

The interferon titre of the preparation is initially $1.5 \times 10^6$ International Units of interferon per ml, its content in proteins is 0.1 mg/ml and its specific activity is $1.5 \times 10^7$ Interferon Units/mg of proteins.

100 ml of the preparation containing the interferon is made to pass through a BLUE DEXTRAN SEPHAROSE column according to Example 1, of 1.6 cm diameter, and containing the gel to a height of 10. cm, operating as in Example 2. After the column has been permeated by the preparation and rinsed, desorption is carried out with an aqueous solution of Tris-HCl, 0.01 M enriched with 1 M NaCl, recovering 6 ml fractions. The interferon is principally recovered in tubes 15 and 16 as shown by the results set out in the table below.

| Tube No. | U.I.F./ml | Proteins (μg/ml) | Specific activity (units of interferon per mg of proteins) |
|---|---|---|---|
| 14 | $2.4 \times 10^5$ | 70 | |
| 15 | $2.3 \times 10^7$ | 111 | $2.1 \times 10^8$ |

-continued

| Tube No. | U.I.F./ml | Proteins (μg/ml) | Specific activity (units of interferon per mg of proteins) |
| --- | --- | --- | --- |
| 16 | $5.8 \times 10^6$ | 12 | $4.8 \times 10^8$ |
| 17 | $2.4 \times 10^5$ | 11 | |
| 18 | $1.2 \times 10^5$ | 10 | |

As indicated above, the products with interferon-type activity are recovered principally in two of the tubes, mainly tubes No. 15 and No. 16.

As compared with the crude preparation, the increase in the specific activity, that is to say the degree of purification, is respectively 15 times for tube No. 15 and 35 times for tube No. 16. The specific activity of tube 16 in particular ($4.8 \times 10^8$ units of interferon per mg of proteins) is up amongst the highest which have ever been published up to the present time.

Furthermore, the recovery of the interferon present in the crude preparation is complete.

In the 100 ml of the starting preparation, there were in toto some $1.5 \times 10^6 \times 100$, and thus $1.5 \times 10^8$, Interferon Units.

Now, having recovered all the products with interferon-type activity in the two 6 ml fractions each will be, respectively:

for tube No. 15: $2.3 \times 10^7 \times 6$ totalling $13.8 \times 10^7$ units
for tube No. 16: $5.8 \times 10^6 \times 6$ totalling $3.4 \times 10^7$ units which is to say, on adding together the values for interferon activity observed in tubes 15 and 16, there are in toto $1.8 \times 10^8$ units.

The remarkable selectivity of the process of the invention should again be emphasised, since it makes it possible simultaneously to enrich the interferon activity while eliminating the major part of the contaminating proteins.

We claim:

1. A process for the separation of products having an interferon-type activity, starting from a preparation containing said interferon-like product comprising contacting said preparation with an adsorbent, equilibrated with the aid of a buffer whose concentration in salt is isomolar or hypomolar as compared with that of blood, said adsorbent comprising on the one hand a gel forming a solid support the size of whose pores is such that it permits the passage of macromolecules, and on the other hand a compound fixed upon the said support, playing the role of ligand vis-a-vis the products to be separated, and possessing the polycyclic structure of the blue chromophore, sold under the trade mark CIBACRON BLUE F3GA, of formula

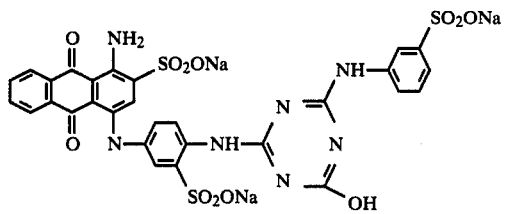

whose configuration makes it possible to retain the interferon in a selective manner, the quantity of adsorbent used and the period of contact between the ligand and the preparation being both sufficient to enable the desired fixation of the products with interferon-type activity.

2. A process according to claim 1, for obtaining purified preparations having an interferon-type activity, characterized by the supplementary step of desorbing the fixed products with the help of a buffer whose concentration in salts is hyper-molar as compared with that of blood.

3. A process according to claim 1, characterized in that the solid support comprises a polysaccharide.

4. A process according to claim 3, characterized by the fact that the ligand, coupled on to the solid support, is CIBACRON BLUE F3GA or CIBACRON BLUE 3GA chromophore.

5. A process according to claim 4, characterized by the fact that said chromophore is attached to a high molecular weight polysaccharide known under the designation DEXTRAN.

6. A process according to claim 1, characterized by the fact that said adsorbent comprises an agarose to which is attached said chromophore blue via the intermediary of a polysaccharide, and which is the product sold under the trade mark BLUE DEXTRAN SEPHAROSE.

7. A process according to claim 1, characterized by the fact that the concentration in salts of the buffer used to equilibrate the adsorbent is less than or equal to 0.15 M.

8. A process according to claim 2, characterized by the fact that the concentration in salts of the desorption buffer is at least 0.5 M.

9. A process for obtaining purified preparations having an interferon-type activity, comprising contacting a complex of products having an interferon-type activity on an adsorbent according to claim 1 with an aqueous solution of a buffer whose concentration in salts is at least 0.5 M, whereby the fixed products are desorbed.

10. A process according to claim 1 characterized by the fact that the contact of said adsorbent and of the preparations to be purified on the one hand and the contact of the fixed products with said buffer on the other hand is carried on in a column of affinity chromatography.

11. A process according to claim 1 characterized by the fact that it is carried on with a fibroblast interferon preparations.

12. A process according to claim 1 characterized by the fact that it is carried on with a leucocyte interferon preparation.

13. A process according to claim 3 wherein the polysaccharide is a modified agarose in which the polysaccharide chains are cross-linked into a three-dimensional sieve.

14. A process according to claim 3 wherein the polysaccharide is an agarose sold under the trademark SEPHAROSE.

15. A process according to claim 5 wherein said polysaccharide has a molecular weight of about 2 million and is known under the designation DEXTRAN 2,000.

16. Products with an interferon-type activity fixed on the adsorbent according to claim 1.

17. A process according to claim 2 characterized by the fact that it is carried on with a fibroblast interferon preparation.

18. A process according to claim 2 characterized by the fact that it is carried on with a leucocyte interferon preparation.

19. A process according to claim 2 characterized by the fact that the contact of said adsorbent and the preparation to be purified on the one hand and the contact of the fixed product with the buffer on the other hand is carried out in a column of affinity chromatography.

20. A process according to claim 1 wherein the solid support comprises a polyacrylamide or an acrylic resin.

* * * * *

UNITED STATES PATENT AND TRADEMARK OFFICE
CERTIFICATE OF CORRECTION

PATENT NO. : 4,172,071
DATED : October 23, 1979
INVENTOR(S) : Edward De Maeyer et al It is certified that error appears in the above-identified patent and that said Letters Patent are hereby corrected as shown below:

Column 2, lines 9 - 19

Column 9, lines 50 - 60:

Delete the formula as shown in each instance and substitute therefor the following formula

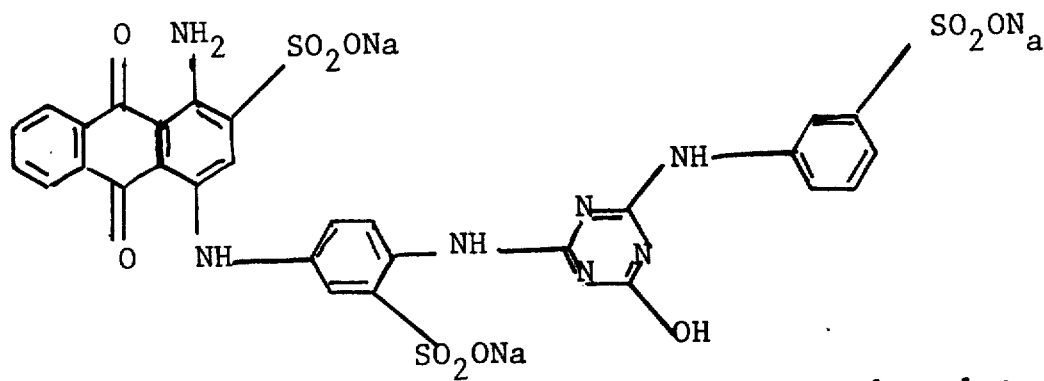

Signed and Sealed this

Twenty-third Day of September 1980

[SEAL]

Attest:

SIDNEY A. DIAMOND

Attesting Officer

Commissioner of Patents and Trademarks